(12) United States Patent
Seibel et al.

(10) Patent No.: US 8,143,600 B2
(45) Date of Patent: Mar. 27, 2012

(54) 3D IMAGING OF LIVE CELLS WITH ULTRAVIOLET RADIATION

(75) Inventors: Eric J. Seibel, Seattle, WA (US); Alan C. Nelson, Gig Harbor, WA (US); Mark E. Fauver, Seattle, WA (US); J. Richard Rahn, Sammamish, WA (US)

(73) Assignee: Visiongate, Inc., Phoenix, AZ (US)

( * ) Notice: Subject to any disclaimer, the term of this patent is extended or adjusted under 35 U.S.C. 154(b) by 1074 days.

(21) Appl. No.: 12/032,959

(22) Filed: Feb. 18, 2008

(65) Prior Publication Data
US 2009/0208072 A1    Aug. 20, 2009

(51) Int. Cl.
*G01N 21/64* (2006.01)
(52) U.S. Cl. .................................................. 250/461.2
(58) Field of Classification Search ............... 250/458.1, 250/459.1, 461.1, 461.2
See application file for complete search history.

(56) References Cited

U.S. PATENT DOCUMENTS

| | | |
|---|---|---|
| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeless, Jr. |
| 3,960,449 A | 6/1976 | Carleton |
| 3,999,047 A | 12/1976 | Green |
| 4,183,623 A | 1/1980 | Haines |
| 4,293,221 A | 10/1981 | Kay |
| 4,360,885 A | 11/1982 | Edgar |
| 4,702,598 A | 10/1987 | Bohmer |
| 4,786,165 A | 11/1988 | Yamamoto |
| 4,858,128 A | 8/1989 | Nowak |
| 4,873,653 A | 10/1989 | Grosskopf |
| 5,034,613 A | 7/1991 | Denk |
| 5,117,466 A | 5/1992 | Buican et al. |
| 5,125,737 A | 6/1992 | Rodriguez et al. |
| 5,141,609 A | 8/1992 | Sweedler |
| 5,159,398 A | 10/1992 | Maekawa et al. |
| 5,281,517 A | 1/1994 | Bacus |
| 5,308,990 A | 5/1994 | Takahashi |
| 5,312,535 A | 5/1994 | Waska et al. |

(Continued)

FOREIGN PATENT DOCUMENTS

JP    02085747 A    3/1990

(Continued)

OTHER PUBLICATIONS

Oldham et al., "Three-dimensional imaging of whole rodent organs using optical computed and emission tomography," 2007, Journal of Biomedical Optics, vol. 12, No. 1, pp. 014009-1 to 014009-10.*

(Continued)

*Primary Examiner* — Kiho Kim
(74) *Attorney, Agent, or Firm* — George A. Leone; Citadel Patent Law (57) ABSTRACT

A method for 3D imaging of cells in an optical tomography system includes moving a biological object relatively to a microscope objective to present varying angles of view. The biological object is illuminated with radiation having a spectral bandwidth limited to wavelengths between 150 nm and 390 nm. Radiation transmitted through the biological object and the microscope objective is sensed with a camera from a plurality of differing view angles. A plurality of pseudoprojections of the biological object from the sensed radiation is formed and the plurality of pseudoprojections is reconstructed to form a 3D image of the cell.

38 Claims, 6 Drawing Sheets

U.S. PATENT DOCUMENTS

| | | | |
|---|---|---|---|
| 5,333,164 A | 7/1994 | Tam | |
| 5,390,023 A * | 2/1995 | Biegen | 356/497 |
| 5,390,226 A | 2/1995 | Tam | |
| 5,402,460 A | 3/1995 | Johnson et al. | |
| 5,428,447 A * | 6/1995 | Toida | 356/601 |
| 5,539,800 A | 7/1996 | Katsevich | |
| 5,548,395 A | 8/1996 | Kosaka | |
| 5,552,605 A | 9/1996 | Arata | |
| 5,644,388 A | 7/1997 | Maekawa et al. | |
| 5,680,484 A | 10/1997 | Ohyama | |
| 5,710,429 A | 1/1998 | Alfano | |
| 5,741,411 A | 4/1998 | Yeung | |
| 5,760,901 A | 6/1998 | Hill | |
| 5,760,951 A | 6/1998 | Dixon | |
| 5,831,723 A | 11/1998 | Kubota | |
| 5,835,617 A | 11/1998 | Ohta et al. | |
| 5,880,838 A | 3/1999 | Marx et al. | |
| 5,936,731 A * | 8/1999 | Cabib et al. | 356/456 |
| 6,026,174 A | 2/2000 | Palcic | |
| 6,037,579 A | 3/2000 | Chan et al. | |
| 6,038,067 A | 3/2000 | George | |
| 6,072,624 A | 6/2000 | Dixon et al. | |
| 6,078,681 A | 6/2000 | Silver | |
| 6,091,983 A | 7/2000 | Alfano et al. | |
| 6,130,958 A | 10/2000 | Rohler et al. | |
| 6,177,277 B1 | 1/2001 | Soini | |
| 6,201,628 B1 | 3/2001 | Basiji | |
| 6,211,955 B1 | 4/2001 | Basiji | |
| 6,215,587 B1 | 4/2001 | Alfano et al. | |
| 6,239,871 B1 | 5/2001 | Gilby | |
| 6,248,988 B1 | 6/2001 | Krantz | |
| 6,249,341 B1 | 6/2001 | Basiji et al. | |
| 6,251,586 B1 | 6/2001 | Mulshine | |
| 6,251,615 B1 | 6/2001 | Oberhardt | |
| 6,291,824 B1 | 9/2001 | Battarbee | |
| 6,312,914 B1 | 11/2001 | Kardos et al. | |
| 6,365,367 B1 | 4/2002 | Friedman et al. | |
| 6,473,176 B2 | 10/2002 | Basiji | |
| 6,519,355 B2 | 2/2003 | Nelson | |
| 6,522,775 B2 | 2/2003 | Nelson et al. | |
| 6,529,614 B1 | 3/2003 | Chao | |
| 6,540,895 B1 | 4/2003 | Spence | |
| 6,591,003 B2 | 7/2003 | Chu et al. | |
| 6,608,682 B2 | 8/2003 | Ortyn et al. | |
| 6,624,930 B1 | 9/2003 | Danner et al. | |
| 6,636,623 B2 | 10/2003 | Nelson et al. | |
| 6,640,014 B1 | 10/2003 | Price | |
| 6,697,508 B2 | 2/2004 | Nelson | |
| 6,741,730 B2 | 5/2004 | Rahn et al. | |
| 6,770,893 B2 | 8/2004 | Nelson | |
| 6,775,399 B1 | 8/2004 | Jiang | |
| 6,842,297 B2 | 1/2005 | Dowski, Jr. | |
| 6,850,587 B1 | 2/2005 | Karimi | |
| 6,944,322 B2 | 9/2005 | Johnson et al. | |
| 6,975,400 B2 | 12/2005 | Ortyn et al. | |
| 7,003,143 B1 | 2/2006 | Hewitt | |
| 7,075,647 B2 | 7/2006 | Christodoulou | |
| 7,141,773 B2 | 11/2006 | Kaplan et al. | |
| 7,197,355 B2 | 3/2007 | Nelson | |
| 7,218,393 B2 | 5/2007 | Sharpe et al. | |
| 7,224,540 B2 | 5/2007 | Olmstead et al. | |
| 7,260,253 B2 | 8/2007 | Rahn et al. | |
| 7,274,809 B2 | 9/2007 | MacAulay et al. | |
| 2002/0122167 A1 | 9/2002 | Riley et al. | |
| 2003/0063384 A1 | 4/2003 | Dowski, Jr. | |
| 2003/0211533 A1 * | 11/2003 | Koishi et al. | 435/6 |
| 2003/0222197 A1 | 12/2003 | Reese | |
| 2004/0008515 A1 | 1/2004 | Brown | |
| 2004/0036875 A1 | 2/2004 | Kramer | |
| 2004/0076319 A1 * | 4/2004 | Fauver et al. | 382/133 |
| 2004/0184648 A1 | 9/2004 | Zhang et al. | |
| 2004/0228520 A1 | 11/2004 | Dresser | |
| 2005/0006595 A1 | 1/2005 | Goodwin et al. | |
| 2005/0085708 A1 | 4/2005 | Fauver et al. | |
| 2005/0085721 A1 | 4/2005 | Fauver et al. | |
| 2006/0023219 A1 | 2/2006 | Meyer et al. | |
| 2006/0066837 A1 | 3/2006 | Ortyn et al. | |
| 2006/0068371 A1 | 3/2006 | Ortyn et al. | |
| 2006/0093200 A1 | 5/2006 | Sharpe | |
| 2006/0132790 A1 | 6/2006 | Gutin | |
| 2006/0171041 A1 | 8/2006 | Olmstead et al. | |
| 2006/0188869 A1 | 8/2006 | Zeskind et al. | |
| 2007/0146873 A1 | 6/2007 | Ortyn et al. | |
| 2007/0215528 A1 | 9/2007 | Hayenga et al. | |
| 2007/0258122 A1 | 11/2007 | Chamgoulov et al. | |
| 2007/0282015 A1 * | 12/2007 | Albert | 514/789 |
| 2008/0020379 A1 * | 1/2008 | Agan et al. | 435/6 |
| 2009/0005676 A1 | 1/2009 | Koenig et al. | |
| 2009/0053247 A1 * | 2/2009 | Deonarain et al. | 424/178.1 |
| 2009/0296744 A1 * | 12/2009 | Dantus et al. | 372/5 |

FOREIGN PATENT DOCUMENTS

| | | |
|---|---|---|
| JP | 10260131 A | 9/1998 |
| JP | 2000121550 A | 4/2000 |
| WO | WO0235474 A1 | 5/2002 |

OTHER PUBLICATIONS

King, M.C. and D. H. Berry, D.H., A Depth Scanning Microscope, Applied Optics, vol. 10, No. 1, Jan. 1971, pp. 208-210.

Bellman, S.H. et al., "ART is Science being A Defense of Algebraic Reconstruction Techniques for Three dimensional Electron Microscopy," Journal of Theoretical Biology 32pp. 205-216, , 1971.

Gilbert, P., Iterative Methods for the Three dimensional Reconstruction of an Object from Projections, Journal of Theoretical Biology 36pp. 105-117, 1972.

Oppenheim, B. E., More Accurate Algorithms for Iterative 3 dimensional Reconstruction, IEEE Transactions on Nuclear Science NS-21pp. 72-77, 1974.

Klug, A., Image analysis and reconstruction in the electron microscopy of biological macromolecules, Chem. Scripta, vol. 14, p. 245, 1979.

Almeida, et al., Fourier transform differences and averaged simularities in diatoms, Applied Optics, vol. 18 No. 10 pp. 1663-1667 (1979).

Miles, C P. et al., "The Use of Optical Fourier Transforms to Diagnose Pleomorphism, Size and Chromatin Clumping in Nuclear Models," Anal Quant Cytol Histol vol. 3 No. 2 pp. 149-156 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Pieper, R.J. and Korpel A., Image processing for extended depth of field, Applied Optics, vol. 22, No. 10, May 15, 1983, pp. 1449-1453.

Ong, S. H., Development of an imaging flow cytometer. Anal Quant Cytol Histol 9(5)pp. 375-382, 1987.

Steward, E. G., Fourier Optics: An Introduction, 2nd ed. (Halsted Press, New York) , 1987.

Kak, A.C. and Slaney, M., Principles of Computerized Tomographic Imaging, IEEE Press, (New York), 1988.

Press , W.H. et al., Numerical Recipes in C (New York: Cambridge University Press), 1988.

Kinney, J. H., "Energy-modulated X-ray Microtomography", Rev. Sci. Instrum. 59(1)pp. 196-197, 1988.

Manglos, S. H. et al., Maximum Likelihood Reconstruction for Cone Beam SPECT: Development and Initial Tests, Physics in Medicine and Biology 34(12)pp. 1947-1957, #1382, , 1989.

Singer, J. R. et al., Image Reconstruction of the Interior of Bodies that Diffuse Radiation, Science 248(4958) pp. 990-993, 1990.

Kinney, J. H., "X-ray Tomographic Microscopy (XTM) Using Synchrotron Ratiation", Annu. Rev. Mater. Sci. 22pp. 121-152, , 1992.

Cheng, P. C., Review on the Development of Cone-beam X-ray Microtomography, Proceedings of the X-ray Optics and Microanalysis, Institute of Physics Ser. No. 130, Kenway, PB, et al. (eds.), Manchester, UK, Aug. 31-Sep. 4, 1992, pp. 559-566.

Kikuchi, S., "Three-dimensional computed tomography for optical microscopes," Optics Communications 107, 432-444, , 1994.

Tiziani, H. J. et al., Three-dimensional analysis by a microlens array confocal arrangements (Applied Optics 33, 567), 1994.

Paulsen, K. D., Spatially Varying Optical Property Reconstruction Using a Finite Element Diffusion Equation Approximation, Medical Physics 22(691-701), 1995.

Shapiro, H. M., Practical Flow Cytometry, 3rd ed., Wiley-Liss, 1995.

Pawley, J. B., Handbook of Biological Confocal Microscopy, Plenum Press, NY 479-490, 1995.

Wedberg, T.C., "Recent results in optical diffraction microtomography," Meas. Sci. Technol., vol. 7, p. 414, , 1996.

Kikuchi, S. et al., "Three-dimensional microscope computed tomography based on general Radon transform for optical imaging systems," Optics Communications 123 (1996) 725-733, 1996.

Bradburn S. et al., Realizations of Focus Invariance in Optical/Digital Systems with Wavefront Coding, Applied Optics, vol. 36, Issue 35, pp. 9157-9166, 1997.

Sheppard, C. J. R. & Torok, P., Effects of specimen refractive index on confocal imaging, Journal of Microscopy, vol. 185, Pt. 3, Mar. 1997, pp. 366-374.

Jorgensen, S. M., "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Taguchi, K. and Aradate, H., "Algorithm for Image Reconstruction in Multi-slice Helical CT", Medical Physics 25(4) pp. 550-561, 1998.

Hampel, U and Freyer, R., Fast Image Reconstruction for Optical Absorption Tomography in Media with Radially Symmetric Boundaries, Medical Physics 25 (1)pp. 92-101, 1998.

Tucker, S.C. et al., Extended depth of field and aberration control for inexpensive digital microscope systems, Optics Express, vol. 4, No. 11, May 24, 1999, pp. 467-474.

Edelmann, P. et al., Correlation of chromatic shifts and focal depth in Spectral Precision Distance Microscopy measured by Micro Axial Tomography, Optical Biopsies and Microscopic Techniques III, Sep. 1999, SPIE vol. 3568, pp. 89-95, 1999.

Marks D. L. et al., Three-dimensional tomography using a cubic-phase plate extended depth-of-field system, Optics Letters, vol. 24, No. 4, Feb. 15, 1999.

George, JS et al., Virtual Pinhole Confocal Microscope, Physics Division Progress Report, wwvv.lanl.gov/p/pdfs/papp_pinhole.pdf, 1999-2000.

Defrise, M. et al., A Solution to the Long-object Problem in Helical Cone-beam Tomography, Physics in Medicine and Biology 45(623-43), 2000.

Sanyal, S. and Ghosh, A., High focal depth with a quasi-bifocus birefringent lens, Applied Optics, vol. 39, No. 14, May 10, 2000, pp. 2321-2325.

Mueller, K. And Yage, R., Rapid 3-D Cone-beam Reconstruction with the Simultaneous Algebraic Reconstruction Technique (SART) Using 2-D Texture Mapping Hardware, IEEE Transactions on Medical imaging 19(12)pp. 1227-1237, 2000.

Endo, M. et al., Effect of Scattered Radiation on Image Noise in Cone Beam CT, Medical Physics 28(4) (469-74), 2001.

Zhao, B. and Dimarzio, C, Differential Interference Contrast (DIC) Microscope Image Processing, The Center for Subsurface Sensing and Imaging Systems (CenSSIS), Northeastern University, Boston, MA.

Chang et al., Enhanced live cell membrane imaging using surface plasmon-enhanced total internal reflection fluorescence microscopy, Optics Express 9308, vol. 14, No. 20, Oct. 2, 2006.

Conchello, J-A., and Dressler, D. E., Extended depth-of-focus microscopy via constrained deconvolution, Journal of Biomedical Optics 12(6), 064026, Nov./Dec. 2007.

Darrell, A. et al., Accounting for Point Source Propagation Properties in 3D Fluorescence OPT, Proceedings of the 28th IEEE, EMBS Annual International Conference, New York City, USA, Aug. 30-Sep. 3, 2006.

Zeskind, B.J., et al., Nucleic acid and protein mass mapping by live-cell deepultraviolet, Nature Methods, published online, 4, 567-569, Jun. 3, 2007; DOI:101038/NMETH1053.

Zeskind, B.J., et al., Nucleic acid and protein mass mapping by live-cell deepultraviolet, Nature Methods, published online, 4, 567-569, Jun. 3, 2007; DOI:101038/NMETH1053 (Supplementary Figures and Text).

Preza, C., et al., Three-Dimensional Transmitted-Light DIC Microscopy, Presented at SPIE's BiOS97; 3D Microscopy: Image Acquisition and Processing IV, 2984-24, 1997.

Zhang, J. et al., Membrane Electric Properties by Combined Patch Clamp and Fluorescence Ratio Imaging in Single Neurons, Biophysical Journal vol. 74 Jan. 1998 48-53.

Curry, A., et al., Epi-illumination through the microscope objective applied to darkfield imaging and microspectroscopy of nanopartide, Jul. 10, 2006, vol. 14, No. 14, Optics Express 6535.

Fauver et al., Development of Micro-Optical Projection Tomography for 3D Analysis of Single Cells, Image Acquisition and Processing XI. Edited by Conchello, Jose-Angel; Cogswell, Carol J.; Wilson, Tony. Proceedings of the SPIE, vol. 5324, pp. 171-181, 2004.

Fauver et al., Three-dimensional imaging of single isolated cell nuclei using optical projection tomography, Optics Exress, May 30, 2005/vol. 13 No. 11/4210-4223.

Suiter, H.R., Apodization for Obstructed Apertures, home.digitalexp.com. , 2001.

Herzenberg, L. A., The History and Future of the Fluoresence Activated Cell Sorter and Flow Cytometry: A View from Stanford, , 2002.

Sharpe, J. et al., "Optical Projection Tomography as a Tool for 3D Microscopy and Gene Expression Studies," Science, vol. 296, pp. 541-545, Apr. 19, 2002.

Xu, Y. et al., Three-dimensional diffuse optical tomography of bones and joints, J. Biomed. Optics, vol. 7, p. 88, 2002.

Widjanarko, T., et al., A post-processing technique for extending depth of focus in conventional optical microscopy, Optics & Laser Technology 34, pp. 299-305, 2002.

Bentley, M. D., The Use of Microcoputed Tomography to Study Microvasculature in Small Rodents, American Journal of Physiology (Regulatory Integrative Comp Physiol) 282(R1267-R1279), 2002.

Martini, N. et al., A new high-aperture glycerol immersion objective lens and its application to 3D-fluoresence microscopy, Journal of Microscopy vol. 206 Pt. 2, May 2002, pp. 146-151, 2002.

Matula, P. et al., "Precise 3D image alignment in micro-axial tomography," Journal of Microscopy, vol. 209, Pt. 2 (Feb. 2003) pp. 126-142, , 2003.

Sharpe, J. et al., Review, "Optical Projection Tomography as a New Tool for Studying Embryo Anatomy," J. Anat. (2003), pp. 175-181, , 2003.

Lane, P.M. et al., Confocal Microendoscopy with Chromatic Sectioning, Spectral Imaging: Instrumentation, Applications, and Analysis II, Proc. of SPIE vol. 4959 pp. 23-26, 2003.

Porras, R. et al., Wavefront coding technology in the optical design of astronomical instruments, 5th Iberoamerican Meeting on Optics and 8th Latin American Meeting on Optics, Lasers, and Their Applications, edited by A. Marcano O., J. L. Paz, Proc. of SPIE vol. 5622, pp. 796-800, 2004.

Forster, B. et al., Complex Wavelets for Extended Depth-of-Field: A New Method for the Fusion of Multichannel Microscopy Images, Microscopy Research and Technique 65:33-42, 2004.

Gao X., et al., Tunable focal depth of an apodized focusing optical system, Optical Engineering 44(6), 063001, Jun. 1-9, 2005.

Miks, A. et al., Theory of hyperchromats with linear longitudinal chromatic, aberration, Proc. of SPIE, vol. 5945, pp. 59450, Y1-Y8, 2005.

Abragamsson, , S. et al., A new approach to extended focus for high-speed, high-resolution biological microscopy, Proc. of SPIE vol. 60900, N1-N8, 2006.

Leitgeb, R. et al., Extended focus depth for Fourier domain optical coherence microscopy, Optics Letters, Doc. ID 69650, Jun. 1, 2006.

Somayaji, M. et al., Enhancing form factor and light collection of multiplex imaging systems by using a cubic phase mask, Applied Optics, vol. 45, No. 13, May 1, 2006, pp. 2911-2923.

Mikula, G. et al., Imaging with extended focal depth by means of lenses with radial and angular modulation, Optics Express, vol. 15, No. 15, Jul. 23, 2007, pp. 9184-9193.

Kerfoot, et al., Christopher A., and Dauffenbach, Lisa M., Quantitative Multiplex Chromagenic Immunohistochemistry, Mosaic Laboratories, www.mosaiclabs.com, Tuscon Symposium, 2007.

Xu, Y. et al., Ultra long high resolution beam by multi-zone rotationally symmetrical complex pupil filter, Optics Express, vol. 15, No. 10, May 10, 2007, pp. 6409-6413.

Long, J.C. et al., Tube Lens Focal Length, Nikon Microscopy U: Interactive Java Tutorials, http://www.microscopy.com, 2007.

* cited by examiner

3D IMAGING OF LIVE CELLS WITH ULTRAVIOLET RADIATION

TECHNICAL FIELD

The present invention relates to optical tomographic imaging systems in general, and, more particularly, to optical projection tomography for 3D microscopy, in which a small object, such as a biological cell, is illuminated with ultraviolet radiation for pseudoprojection imaging and reconstruction into a 3D image.

BACKGROUND

Advances in imaging biological cells using optical tomography have been developed by Nelson as disclosed, for example, in U.S. Pat. No. 6,522,775, issued Feb. 18, 2003, and entitled "Apparatus and method for imaging small objects in a flow stream using optical tomography," the full disclosure of which is incorporated by reference. Further developments in the field are taught in Fauver et al., U.S. patent application Ser. No. 10/716,744, filed Nov. 18, 2003 and published as US Publication No. US-2004-0076319-A1 on Apr. 22, 2004, entitled "Method and apparatus of shadowgram formation for optical tomography," (Fauver '744) and Fauver et al., U.S. patent application Ser. No. 11/532,648, filed Sep. 18, 2006, entitled "Focal plane tracking for optical microtomography," (Fauver '648) the full disclosures of which are also incorporated by reference.

Processing in an optical tomography system begins with specimen preparation. Typically, specimens taken from a patient are received from a hospital or clinic and processed to remove non-diagnostic elements, fixed and then stained. Stained specimens are then mixed with an optical gel, inserted into a microcapillary tube and images of objects, such as cells, in the specimen are produced using an optical tomography system. The resultant images comprise a set of extended depth of field images from differing perspectives called "pseudoprojection images." The set of pseudoprojection images can be reconstructed using backprojection and filtering techniques to yield a 3D reconstruction of a cell of interest. The ability to have isometric or roughly equal resolution in all three dimensions is an advantage in 3D tomographic cell imaging, especially for quantitative image analysis.

The 3D reconstruction then remains available for analysis in order to enable the quantification and the determination of the location of structures, molecules or molecular probes of interest. An object such as a biological cell may be labeled with at least one stain or tagged molecular probe, and the measured amount and location of this biomarker may yield important information about the disease state of the cell, including, but not limited to, various cancers such as lung, breast, prostate, cervical, stomach and pancreatic cancers.

The present disclosure allows an extension of optical projection tomography to live cell imaging and is expected to advance cell analysis, drug development, personalized therapy, and related fields. Until now, live cell microscopy has traditionally been done by non-labeling 2D imaging techniques such as phase contrast, DIC, and polarization contrast microscopy.

Native absorbance and fluorescence imaging using deep ultraviolet (DUV) at 250 nm to 290 nm wavelengths has been technically challenging and causes phototoxicity in irradiated cells. More recently, vital stains have been used that typically emit fluorescence signals for 3D live cell imaging, because commercial microscopes (of confocal, deconvolution, and multiphoton excitation varieties) rely on fluorescence for building up multiple planar slices for generating 3D images. However, in these cases, the 3D image resulting from a stack of 2D images has about four times less axial resolution as the lateral resolution within each slice, thereby making quantitative analysis imprecise. The ability to have isometric or roughly equal resolution in all three dimensions is a significant advantage in 3D tomographic cell imaging, especially for quantitative image analysis.

One advantage of using DUV illumination for live cells is that native DNA and protein absorb the light at 260 nm and 280 nm, respectively, without the use of any photochemical label that must permeate the cell membrane and sometimes the nuclear membrane of the cell, which is in a non-normal state. Furthermore, the label or stain is only an intermediary step toward the measurement of target protein or nucleotide (DNA) which adds a large degree of variability in this measurement. Elimination of such exogenous species would potentially improve the accuracy of a quantitative measure of protein or nucleotide (DNA), as well as reduce time, effort and complexity by eliminating steps in the sample preparation. Unfortunately, the use of DUV illumination has demonstrated phototoxicity in the past, due to the high dose of radiation required to stimulate a strong signal.

Recently, however, DUV imaging of live cultured human and mouse cells was demonstrated at 260 nm and 280 nm using DUV light-emitting diodes (LEDs) (See, for example, Zeskind, B J, et al., "P. Nucleic acid and protein mass mapping by live cell deep ultraviolet microscopy," Nature Methods 4(7):567-569 (2007)).

The present disclosure describes a new, novel and surprisingly effective 3D imaging system that provides solutions to long felt needs in the field of DUV 3D imaging of cells, and more particularly, live cells.

BRIEF SUMMARY OF THE DISCLOSURE

A method for 3D imaging of cells in an optical tomography system is provided including moving a biological object relatively to a microscope objective to present varying angles of view. The biological object is illuminated with optical radiation having a spectral bandwidth limited to wavelengths between 150 nm and 390 nm. Radiation transmitted through, scattered by, or secondarily emitted by the biological object and captured by the microscope objective is sensed with a camera to record images from a plurality of differing view angles. A plurality of pseudoprojection images of the biological object from the sensed radiation is formed and the plurality of pseudoprojections is reconstructed to form a 3D image of the cell.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for imaging an object of interest. Several features of methods and systems in accordance with example embodiments of the invention are set forth and described in the Figures. It will be appreciated that methods and systems in accordance with other example embodiments of the invention can include additional procedures or features different than those shown in Figures. Example embodiments are described herein with respect to biological cells. However, it will be understood that these examples are for the purpose of illustrating the principals of the invention, and that the invention is not so limited.

Additionally, methods and systems in accordance with several example embodiments of the invention may not include all of the features shown in these Figures. Throughout the Figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally as used herein the following terms have the following meanings when used within the context of optical microscopy processes:

"Capillary tube" has its generally accepted meaning and is intended to include transparent microcapillary tubes and equivalent items with an inside diameter generally of 500 microns or less.

"Depth of field" is the length along the optical axis within which the focal plane may be shifted before an unacceptable image blur for a specified feature is produced.

"Object" means an individual cell, item, thing or other entity.

"Pseudoprojection" includes a single image representing a sampled volume of extent larger than the native depth of field of the optics. The concept of a pseudoprojection is taught in Fauver '744.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

With respect to imaging of live cells, several assumptions are made in this disclosure: (1) submicron isometric resolution is required of the chromatin structure in the nucleus which limits the wavelength of optical radiation to frequencies higher than infrared (less than or equal to near infrared wavelengths, <1000 nm), (2) individual cells are being imaged or possibly analyzed which may allow for diffraction measurement at multiple perspectives, and (3) harvesting of the cell after imaging is desired with minimal cell damage.

Figure 1:
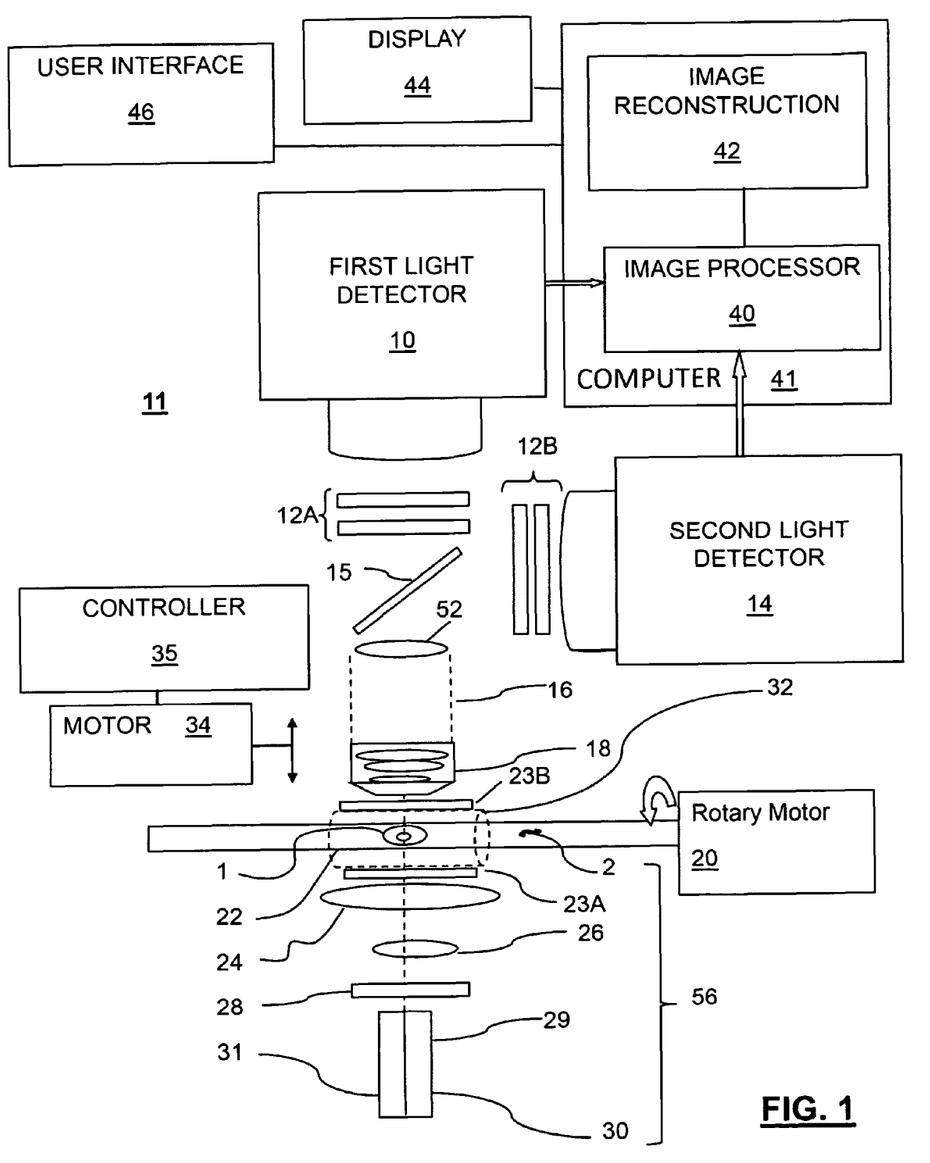
FIG. 1 schematically shows an example of a system for 3D imaging of cells in an optical tomography system employing ultraviolet radiation.

Referring now to FIG. 1 a system for 3D imaging of cells in an optical tomography system 11 employing ultraviolet radiation is schematically shown. A tube 22, such as a capillary tube, microcapillary tube or equivalent, is positioned to be viewed by a microscope 16 including a microscope objective 18 and a tube lens element 52. A rotation mechanism, for example, a rotary motor 20 is attached to the tube 22. An axial translation mechanism, for example motor 34, is coupled to the microscope objective. A radiation source 29 is positioned to illuminate a part of the tube 22 including a biological object 1 held therein. The radiation source 29 generates radiation having a spectral bandwidth limited to wavelengths between 150 nm and 390 nm. In one useful example, the radiation source 29 comprises multiple sources 30, 31 transmitting at least two selected wavelengths that are detected concurrently by a first light detector 10 and a second light detector 14. Optional filters 12A, 12B are selected to block fluorescence having a wavelength longer than the UV limited spectral bandwidth, such as native tryptophan fluorescence, and/or increase separation of differing ultraviolet radiation signals. The radiation source may advantageously be incorporated into a computer-controlled light source and condenser lens assembly 56. The computer-controlled light source and condenser lens assembly 56 may further include condenser lens optics 24, 26 a light diffuser 28 and the radiation source 29.

In one example embodiment, the tube 22 is placed in a viewing area between two optically flat surfaces such as a standard microscope slide 23A and a standard microscope coverslip 23B. The interstices between the tube 22 and the microscope slide 23A and coverslip 23B are filled with optical gel 32 or an equivalent material such as inorganic and organic oils, having an index of refraction that also substantially matches those of the tube 22, and the microscope slide and coverslip. The tube 22 itself may advantageously be coated with an oil of similar optical properties. The outer diameter of the tube 22 may be, for example about 250 microns. Although not always shown in order to simplify the drawings for clarity, it will be understood that refractive index matching materials are used to match optics in the various embodiments described herein. A typical refraction index, n, matched to capillary tubing used in an optical tomography system is about 1.48, for example, at 590 nm, but the dispersion curve moves sharply upward in the UV. Estimated refractive index of fused silica capillary tube is 1.51 at 250 nm, and transmittance of DUV by UV grade fused silica is about 90%.

The biological object 1 may advantageously be selected from the group consisting of a cell, a live cell, a fixed cell, an unfixed cell, a frozen cell, a thawed cell, a desiccated cell, a cloned cell, a mobile cell, an immobilized cell, an encapsulated cell, a cell nucleus, cell parts, an organelle, a sub-cellular component, chromosomes, and equivalent materials. The optical tomographic imaging system 11 may advantageously employ illumination radiation having a frequency that stimulates native fluorescence from the biological object, where the light detectors and image processor further include modules for measuring the stimulated fluorescence. The biological object is contained in aqueous environment 2. The aqueous environment 2 comprises physiological buffered saline or other solutions as described below.

A beamsplitter 15 is positioned to split radiation transmitted through the biological object into at least two selected wavelengths. The beamsplitter may advantageously be selected from the group consisting of a polarizing beam splitter, a Wollaston prism, a birefringent element, a half-silvered mirror, a 50/50 intensity beamsplitter, a dielectric optically coated mirror, a pellicle film, a dichroic beamsplitter, mirror, prism, diffractive optical element, grating, and equivalents. The first light detector 10 is positioned to sense radiation transmitted through the biological object 1, the microscope objective 18, the beamsplitter 15 and a first set of the optional filters 12A. Similarly, the second light detector 14 is positioned to sense radiation transmitted through the biological object 1, the microscope objective 18, the beamsplitter 15 and a second set of the optional filters 12B. In one example, the first and second light detectors 10, 14 may each particularly include a pixel array detector sensitive to ultraviolet light, where each pixel array detector is selected to detect a different one of the two selected wavelengths.

A computer 41 includes an image processor 40 coupled to receive data from the first and second light detectors 10, 14. A reconstruction module 42 is coupled to the image processor 40, where the reconstruction module processes the data to form a 3D image of the cell using reconstruction algorithm techniques such as taught in Fauver '744 for example. The image processor 40 transmits processed image data to the 3D image reconstruction module 42 which may advantageously be coupled to an optical display 44 for operator viewing. User interface 46 can be provided for operator control and information purposes. The user interface 46 may be a GUI interface or the like coupled to the computer 41.

In one example, the axial translation mechanism 34 comprises a piezoelectric transducer or equivalent device. A controller 35 linked to control the piezoelectric transducer may advantageously be a computer, computer module or the like, where the piezoelectric transducer is controlled to axially move the objective lens 18.

In one example system, the optical tomographic imaging system 11 is configured through use of filters and radiation sources to image cells using wavelengths limited to between 240 nm and 300 nm. Radiation detected by the first detector 10 may have wavelengths primarily in a first range between 260 nm and 265 nm. Radiation detected by the second detector 14 may have wavelengths primarily in a second range between 280 nm and 285 nm. The first range operates to enhance natural radiation absorbance by DNA and RNA. The second range operates to enhance natural radiation absorbance by protein. The first and second wavelength ranges may be provided using a pair of radiation sources, each source transmitting one of the two selected of wavelength ranges. One of the detectors may be tuned to detect absorbance around 270 nm near hydrophilic surfaces such as DNA and protein.

In one embodiment the radiation may be measured in time series using time to separate signals. The radiation source may be pulsed in a time series to cause pulsed excitation of the cells in order to increase signal to noise, separating signals. For example, a radiation source at 260 nm may be pulsed at a time, $T_0$, followed by a 280 nm pulse at $T_1$, followed in turn by one or more laser pulses at n subsequent time increments, $T_n$, where n is any number denoting a subsequent point in time.

Alternatively, the native tryptophan fluorescence can be measured to obtain a secondary measure of protein and its confirmation and constituents, such as amino acids. A third beam splitter would be required unless time series illumination is used. In this alternative design, beamsplitter 15 would split all DUV light (240-300 nm) to the DUV light detector 14 while the lower frequency fluorescence signal would be detected by a fluorescence light detector 10 (>300 nm). Operation of DUV light sources 30, 31 can be in time-series so radiation absorbance primarily by nucleotides (260-265 nm) can be captured at time $T_0$ while radiation absorbance primarily by amino acids (280-285 nm) can be captured at time $T_1$ using the same detector 14. Discussion of filters 12A, 12B is warranted in this example as the set before the fluorescence detector will be the standard long-pass fluorescence emission filters while the set before the DUV detector will be DUV band pass filters or short-pass fluorescence blocking filters.

In yet another example, laser light is incident at an oblique angle relative to the objective lens optical axis, blocking the unscattered light and allowing dark-field measurement of the scattering profile at higher scattering angles. One example of the use of laser scattering at visible wavelengths may be found in U.S. Pat. No. 6,741,730, issued May 25, 2004 to Rahn, entitled "Method and Apparatus for Three-Dimensional Imaging in the Fourier Domain," which is incorporated herein by reference.

In still another example, laser illumination parallel to the optical axis is used. A disk of absorbing material is located in the back focal plane of the objective. The diameter of the absorber is only large enough to block unscattered and very low-angle scattered light. The resulting annular aperture permits a dark-field measurement of the scattering profile at higher scattering angles.

In still another example, live stain, either absorbance or fluorescence, in standard bright-field transmission mode (removing diffraction analysis) or antibody/probe and nanoparticle is used in dark-field illumination mode for molecular specific labeling of proteins and/or DNA in the living cell.

In operation the image reconstruction module 42 determines a size of a voxel in the reconstructed 3D image. The reconstruction module 42 may further include a module constructed in accordance with known software engineering techniques for measuring a concentration of molecules absorbing the radiation by measuring the absorbance per voxel.

In one useful embodiment, the optical tomographic imaging system 11 lends itself nicely to DUV absorbance imaging. Using LEDs at 260 nm and 280 nm with bandwidths of 20 nm allows for simple and robust instrumentation without need for excitation filters. The condenser optics 56 may include, for example, a DUV condenser lens (for example, model UV-Kond, from Zeiss, Germany) and objective lens 18 may comprise a lens such as available from Zeiss, 100×, 1.25 NA, Ultrafluar, or a custom 265 nm objective lens, as available from Optics Technologies, Inc., Rochester, N.Y. To block the ambient and fluorescent light, filters 12A, 12B may include a band pass filter with a bandpass from 250 nm to 290 nm as available from Chroma Technology Corp. or Omega Optical, both of Brattleboro, Vt., before light reaches the UV sensitive CCD camera. Useful CCD cameras include CCD cameras from Sony Corporation of Japan, the PhotonMax model camera from Princeton Instruments, Trenton, N.J., or devices from Sarnoff Imaging, Princeton, N.J.

Live cell imaging often requires the specimen stage and glycerol, oil, or water-immersion objective lens to be temperature controlled. To convert from 2D DUV imaging to 3D Cell-CT DUV imaging, the materials must be UV transparent for the short transmission distances (path lengths) required for imaging isolated cells in a microcapillary tube of 50 microns in diameter. For example, the cell medium should be a physiological buffer solution that may have higher refractive index to help match to the cell plasma membrane. Additives to the aqueous solution may include, but are not limited to, polyethylene glycol (PEG), glycerol, modified or derivative PEGs, and agarose gel. When the cell medium cannot be well matched to the glass used for the microcapillary tube, then increasing the inner diameter may help reduce the degree of refraction at the inner tube wall. The refractive index should be able to be matched well with the outer tube wall since no biocompatibility needs to be addressed. However, materials that do not fluoresce within the wavelength range of signal 250 nm-290 nm should be considered when the rotational joint is being selected.

Figure 2:
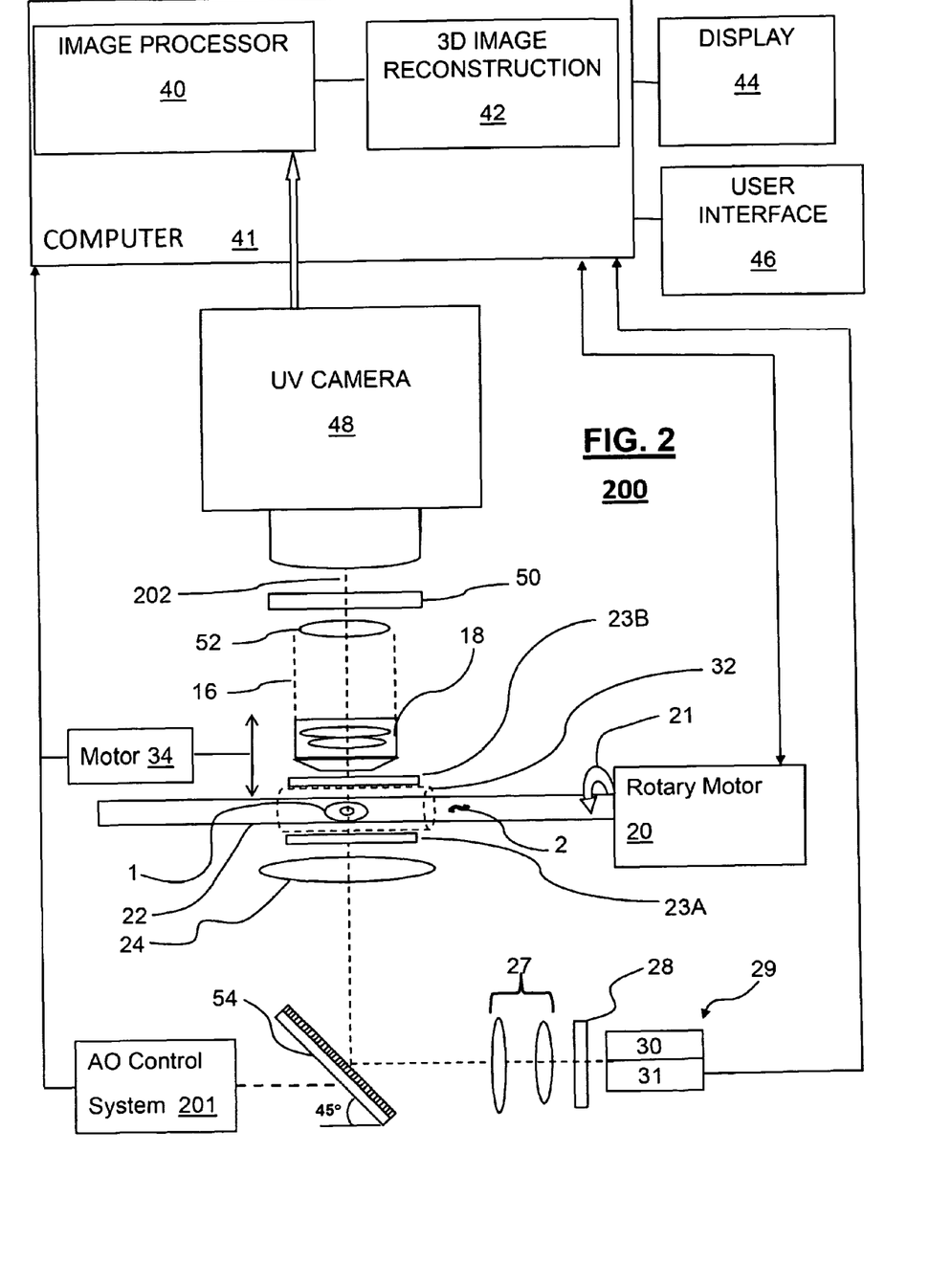
FIG. 2 schematically shows an alternate example of a system for 3D imaging of cells in an optical tomography system with ultraviolet radiation using a UV camera and optional adaptive optics.

Referring now to FIG. 2 an alternate example of system for 3D imaging of cells in an optical tomography system with ultraviolet radiation using a UV camera and optional adaptive optics is schematically shown. The requirement for live cell imaging imposes a restriction on the types of aqueous and physiological buffer solutions and thus on the range of refractive index that can be used around the cell. This embedding medium surrounding the cell and within the tube is expected to have sufficient refractive index mismatch with standard dry or oil immersion microscope objectives to cause aberrations in the resulting images. Compensation for this index mismatch can be designed for a specified imaging depth or distance from objective lens to cell that contains physiological buffer. However, even low-order spherical aberration varies with the variation in axial depth, so dynamic compensation of optical wavefront distortion is advantageous for microscopic imaging across axial depths. This technique of dynamic distortion control or compensation is referred to as adaptive optics. The optical component used for such dynamic aberration compensation is often a spatial light modulator or a deformable membrane mirror. An adaptive reflection mirror is the preferred component in a DUV microscope due to the non-optimal transmission properties of DUV light through sophisticated optical components.

A system for 3D imaging of cells 200 includes several components that are the same as or similar to those described above with respect to FIG. 1. As described above, a tube 22 is positioned relative to a microscope objective 18 for viewing an object of interest 1. As described above, a microscope 16 includes an objective lens 18 and a tube lens element 52. The microscope objective 18 is aligned along an optical axis 202. In contrast to the system of FIG. 1, only a single ultraviolet (UV) camera 48 is used for acquiring images of the object of interest. The UV camera 48 is also aligned along the optical axis 202. Interposed between the UV camera 48 and the tube lens element 52 is a fluorescence-blocking filter 50. As above, the fluorescence blocking filter 50 is selected to block longer wavelength fluorescence and/or increase separation of differing ultraviolet radiation signals.

The aqueous environment 2 and object of interest 1 may cause a sufficiently large refractive index mismatch between microscope objective 18 and tube 22 and optical gel 32 or equivalent to necessitate the use of an adaptive mirror 54 with associated adaptive optics (AO) controller 201 to reduce depth-dependent image aberrations. This adaptive optics component can be an optional element located between the radiation source 29, optical elements 27 and condenser lens 24. Whether unpowered or energized at a constant wavefront compensation (2D) profile, the adaptive mirror 54 becomes a static 90-degree turn in the optical system that may compensate for a single depth level.

As described above, images from the UV camera 48 are transmitted to the image processor 40. The image processor transmits processed image data to the 3D image reconstruction module 42 which may advantageously be coupled to the optical display 44 for operator viewing if desired. User interface 46 is provided for operator control and information purposes. The user interface 46 may be a GUI interface or the like.

Figure 3:
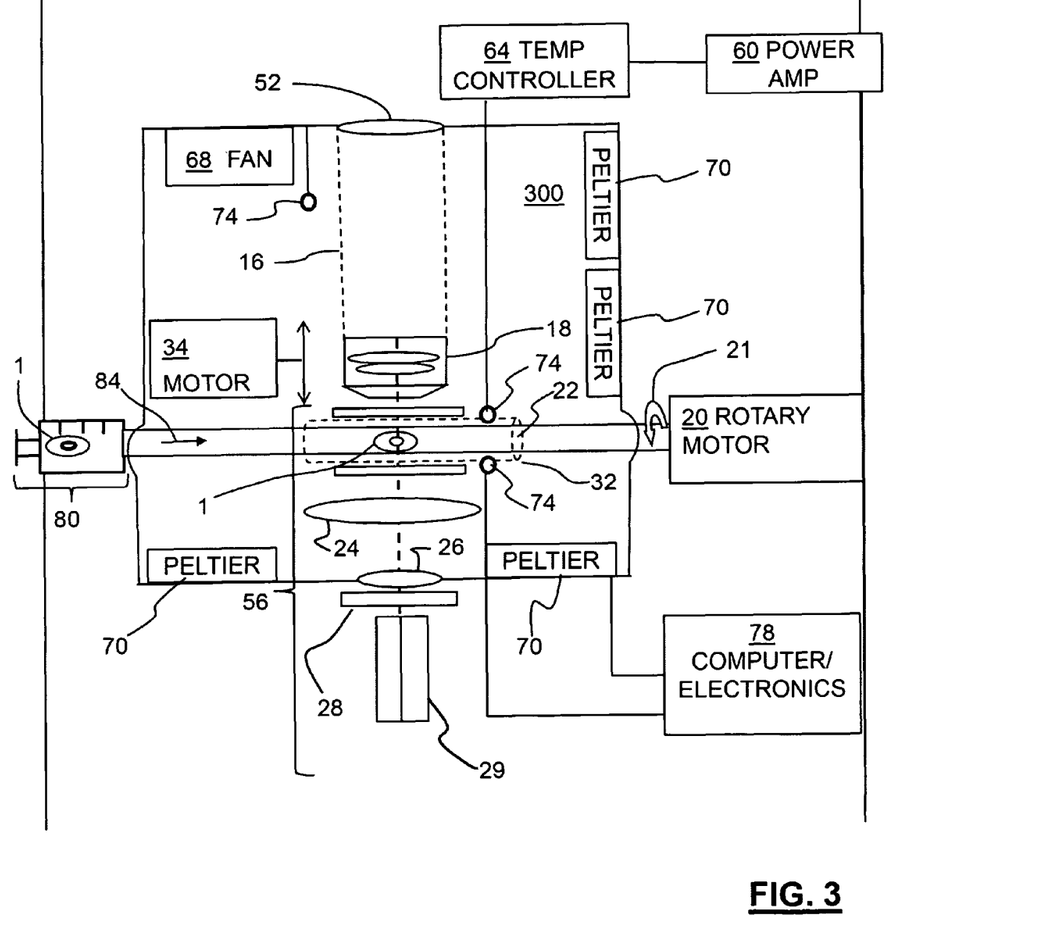
FIG. 3 schematically shows an embodiment of a temperature-controlled housing for use in an optical tomography system.

Referring now to FIG. 3, an embodiment of a temperature-controlled housing for use in an optical tomography system is schematically shown. A temperature-controlled housing 300 contains an object of interest, such as a biological cell 1, or other biological material, is contained in a tube, capillary tube, or microcapillary tube 22, that is positioned relative to a microscope objective 18. The microcapillary tube 22 is rotatable by a rotary motor 20 to allow controlled rotational motion 21 of the cells 1 within the microcapillary tube 22. The cell 1 and gel 32 can be advanced within the capillary tube 22 along the horizontal axis by positive pressure applied, for example, by a syringe 80. Another motor 34 controls vertical axial movement of the microscope objective 18, and tube lens 52. The microcapillary tube 22 is encased within optical gel or refractive index matching medium 32 and is part of and atop of the sample-condenser light assembly 56.

A power amplifier 60 provides energy for the temperature controller 64 that responds to at least one sensor 74 and that may be further regulated with computer and electronic input 78 to maintain the desired temperature within specified ranges, such as 5 to 39 degrees C. However, to maintain functions approaching physiological levels, a warm-blooded animal cell such as a human requires tight temperature control, i.e. 36 degrees C. with range of +/−0.5 degrees C. Regulation of temperature as well as microfluidic conditions facilitates keeping cells alive (i.e. especially labile normal or abnormal cells, pre-cancerous, cancerous, viral infected; or other pathogenic cell populations). In one example, three sensors 74 are positioned near the microscope head 16 and above and below the microcapillary tube 22. An optional internal fan 68 for air circulation is present in some embodiments to aid in temperature control. Peltier thermoelectric heaters/coolers 70 may be positioned in throughout the system and may be positioned both above and below the microcapillary tube 22 provide thermal energy for fine temperature control. Additional locations for Peltier heaters/coolers 70 may be advantageous in specific embodiments. Alternatives to thermoelectric heater/coolers and fans are the options of temperature controlled water circulator or equivalents around a chamber that encloses the microscope. In some embodiments temperatures of about 35 degrees C. to about 36 degrees C. are used, in others higher or lower temperatures may facilitate study of specific biological processes or for use of specific reagents in living cells.

Having described the optical tomography system in detail above, a description of the operation of the system will now be presented in order to aid understanding of the disclosure. Biological objects 1, such as living cells, are injected into the microcapillary tube 22 via the syringe device 80 where pressurized capillary flow 84 moves the biological objects 1 to a viewing window beneath the objective lens 18 of the microscope 16. At least one radiation source 29 (e.g. DUV and visible light) is positioned to illuminate a part of the microcapillary tube 22 that includes the biological objects 1. In some embodiments the radiation wavelengths of about 260 nm to about 280 nm are used. The radiation passes through the light diffuser 28 and condenser lens assembly 24, 26, as part of the sample-condenser light assembly 56. The integrated sensors 74, temperature controller 64 and fan 68 maintain the temperature to maintain and increase cell viability. The system allows numerous variations to study living cells under defined and controlled conditions.

The optical tomography system described above and elsewhere uses temperature control and microfluidics to maintain suitable conditions such that any living biological material may be examined including, but not limited to, cells from humans, as well as cells from any other species. The cells, or other biological material, flow through one or more tubes (e.g. microcapillary tubes) to facilitate imaging. In some embodiments the microcapillary tube 22 comprises a straight tube of more than one channel. It is recognized that the optical tomography system may be used to harvest cells or subcellular material in certain embodiments.

In some embodiments the system senses radiation including imaging signals emanating from macromolecular complexes, nucleoprotein, DNA, RNA, or protein, comprised in living cells, or in some cases non-living cells, or fragments thereof. Cells comprising component DNA, RNA, and protein complexes may be treated with chemicals, biological agents, including, but not limited to biologically active molecules, nanoparticles, modified nanoparticles, microspheres, protein protocells, antibodies, biomarkers, cytokines, other nucleotides, other proteins, or alternately mechanically manipulated by micromanipulation or other treatments (e.g. transfection reagents, viruses, liposomes, and like agents) to alter or facilitate molecular uptake or affect other cellular processes during the imaging process. Biological or chemical agents may be labeled or modified with chromophores and fluorophores. Embodiments also use nanoparticles that are modified by labeling with gold, colloidal gold, iron, and iron oxide, and like molecules that have absorption, fluorescence, and scattering properties acting as optical contrast mechanisms in the 3D image or diffraction pattern. Use of nanoparticles and microspheres in addition to chromophores and fluorophores allows enhanced 3D contrast. For example, cells could be treated with agents that affect the cell cycle, cellular differentiation, infectivity, reduce or increase pathogenicity, or the cells can be further manipulated to alter sub-cellular compartmentalization. The expression and display of cell surface biomarkers or chromatin or other cellular nucleoprotein or macromolecular complexes could be examined during all or some of these treatments.

In certain embodiments the living cells or other biological material are illuminated with multiple wavelengths of radiation. In such cases, a plurality of pseudoprojection images of the cell, or other biological material that are formed from the computer processing of input images may be processed using ratio imaging techniques. In some embodiments the ratio imaging includes images formed from radiation wavelengths of about 260 nm to about 280 nm.

Alternately, in some cases, live cell staining techniques including, but not limited to fluorescence and laser diffraction may be used to advantage for obtaining images.

Figure 4:
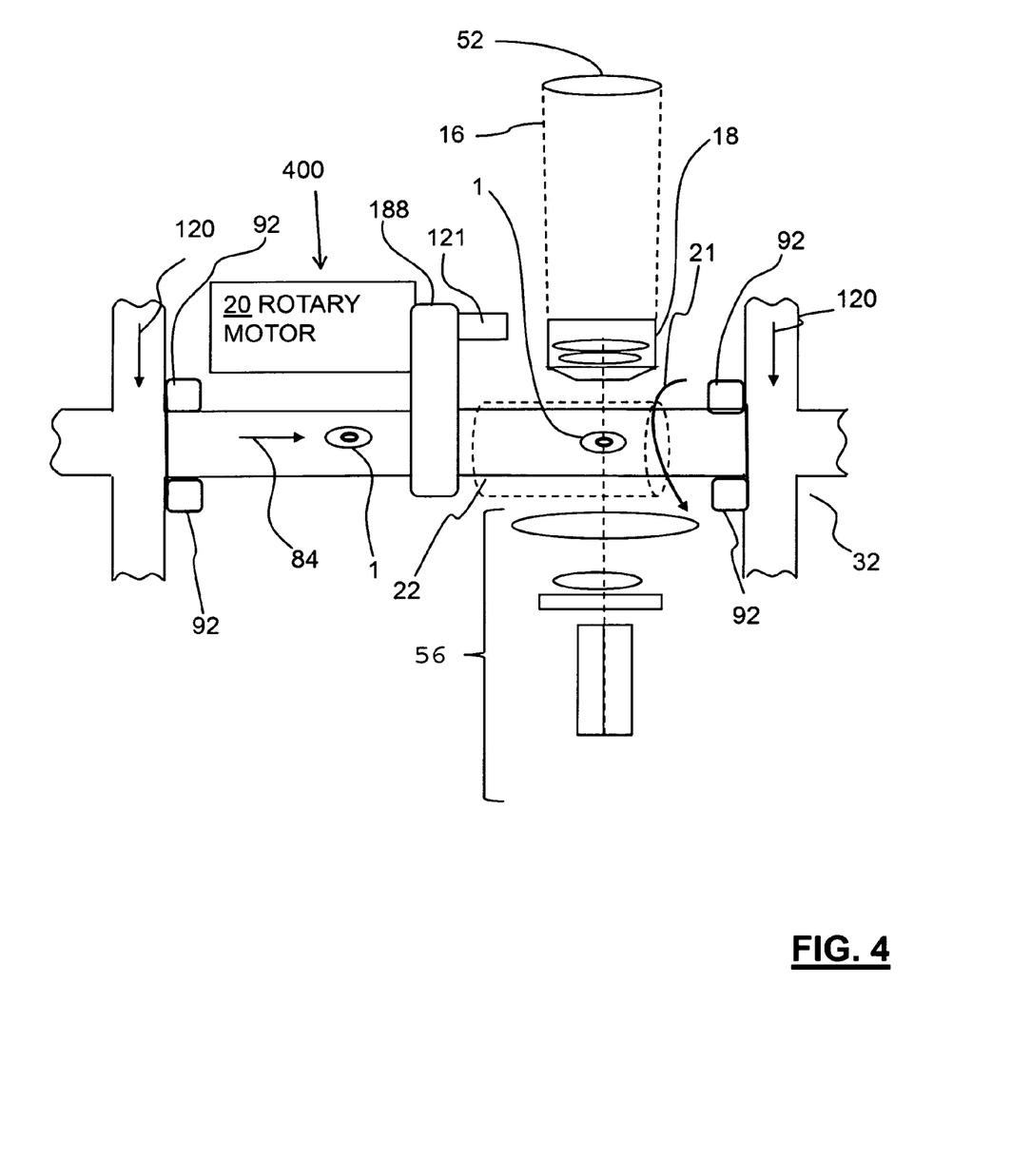
FIG. 4 schematically shows a side view of an example of a microfluidics cartridge as used in a raceway configuration for imaging cells.
Figure 5:
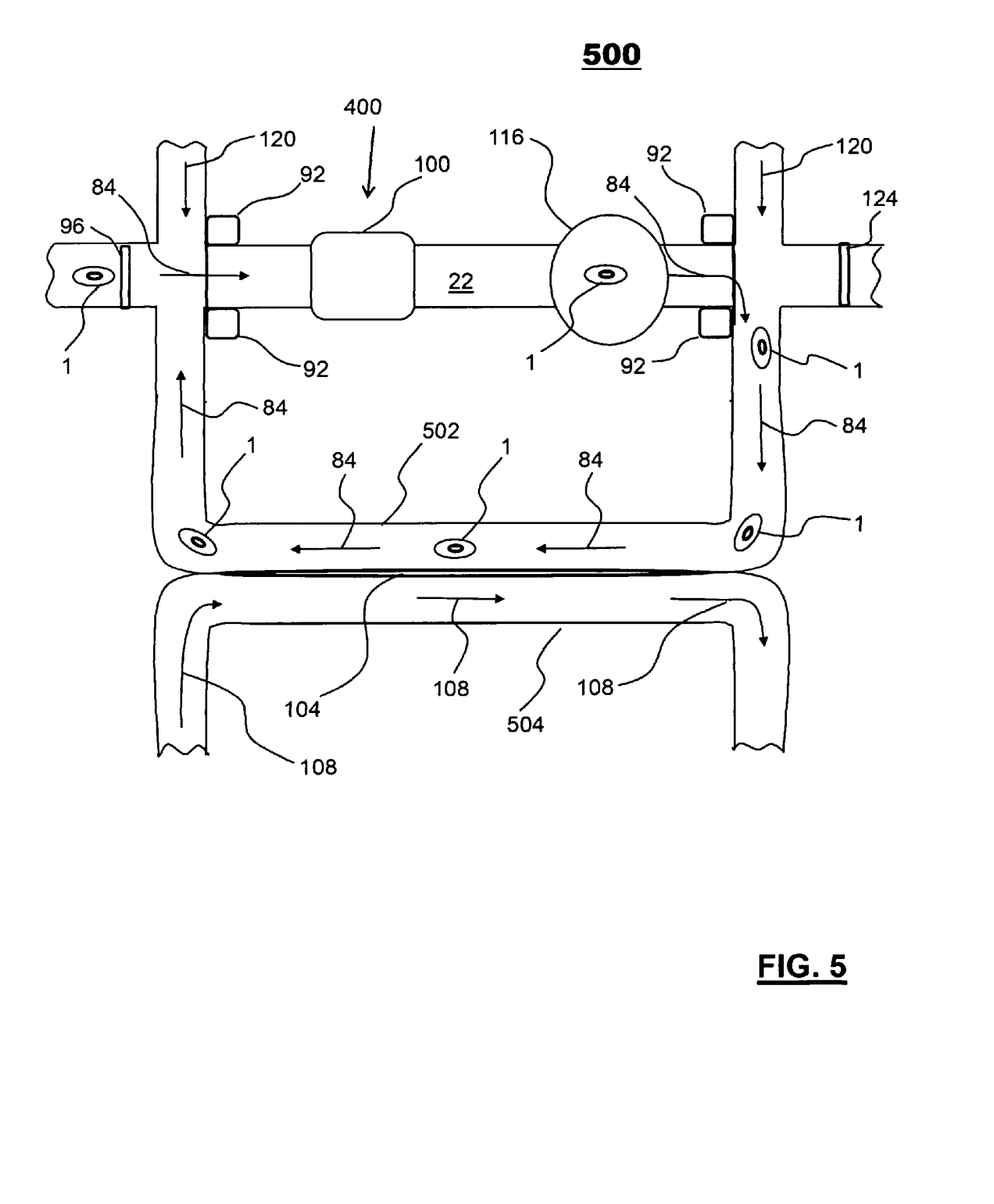
FIG. 5 schematically shows a top view of an example of a microfluidics cartridge as used in a racetrack configuration for imaging cells.

Referring now to FIG. 4, a side view of an example of a microfluidics cartridge 400 is schematically shown. A rotary motor 20 includes a shaft 121 coupled to turn a belt 188, where a second end of the belt 188 is coupled to rotate a microcapillary tube 22. The microfluidics cartridge operates with positive pressure and negative pressure to move the cells in a raceway with a secondary channel to supply nutrients and oxygen, remove metabolic waste, and allow drugs to interact with cells in physiological buffer (as best shown in FIG. 5). A bearing or friction fit 92 allows the microcapillary tube 22 to rotate while an object, such as a cell, passes through the tube. A microscope 16 including condenser illumination assembly 56 is positioned proximate the cartridge to view the object along the optical axis of the microscope 16.

Referring now to FIG. 5, a top view of an example of a microfluidics cartridge as used in a racetrack configuration for imaging cells is schematically shown. The microfluidics cartridge 400 is coupled in a fluidic racetrack configuration 500. The racetrack configuration includes an imaging area 116 along the optical axis of the objective lens including an optical window. Also included is an entrance valve 96, an exit valve 124 and a first channel 502. The first channel 502 is in fluid communication with a secondary channel 504. The channels may be joined, for example, with a semi-permeable membrane 104. The entire racetrack is maintained in a temperature controlled environment such described herein with respect to FIG. 3 using Peltier heater/cooler elements or equivalents.

Fresh nutrients, oxygen, buffer (pH, osmolarity, etc), optional drugs and the like as needed to maintain cell viability may be introduced through the secondary channel 504 as indicated by flow arrows 108. However, if microfluidic conditions are right, then the cells won't move laterally, only axially through the first channel 502 while diffusion allows fresh nutrients such as $O_2$, buffer materials and metabolic waste to move and thus mix along concentration gradients. In one example, the semi-permeable membrane 104 may be replaced by a joined channel with non-turbulent parallel flows allowing diffusion of small molecules and solutions while maintaining cells within their original streamlines of microfluidic flow. Shear stress within physiological range is possible with slow flow rates while channel geometry, fluid viscosity, temperature, and cell type also play a role.

In operation cells are injected through entrance valve 96 into the microfluidics cartridge 400. A trough 100 serves as a housing for the rotation motor and belt used to rotate the microcapillary tube 22 while cells travel through the tube. Positive and negative pressure 120 is applied to control pressurized flow 84 throughout the racetrack. After imaging, a an exit valve 124 can be used to direct selected cell 1 by flowing fluid into a discard channel or for harvesting the live cell.

The specimen being examined may be a biopsy from a fine needle aspirate (FNA). The resulting sample of live cells may be split into several different racetracks with separate entrance valves (not shown). Each sub-sample being examined may be exposed to different drugs (such as drug A, drug B, drug combination A+B, and control—no drug), and the response may be monitored as real-time feedback for the purpose of personalized drug response for the patient.

In one example, the racetrack configuration is useful as a research/drug discovery instrument. In operation, live cells may be circulated in the racetrack while imaging in 3D. Each live cell in the sample may be exposed to a chemical and environmental protocol and small changes in cellular response may be indicative of a desired cell type. Variations is apoptosis, mitosis, necrosis, secretion, and other programmed cell responses to stimuli can be measured at high sensitivity in real-time. When the live cells exhibit desired characteristics, the cells may be harvested. One such harvesting method is disclosed in co-pending US patent application to Hayenga, entitled, "Cantilevered coaxial flow injector apparatus and method for sorting particles," and published on Sep. 20, 2007 under publication number US 2007-0215528 A1, the full disclosure of which is incorporated herein by reference.

In some alternative embodiments, labeled nanoparticles like antibody/DNA labeling of gold or nanospheres can be used with live cells to label specific proteins, chromatin, and DNA. For example, gold nanoparticles or colloidal gold have both absorption and scattering contrast and are biocompatible with living cells. Fluorescently-labeled nanospheres and microspheres can have absorption, fluorescence, and scattering as optical contrast mechanisms in the 3D image or diffraction pattern. Using nanoparticles in addition to chromophores and fluorophores will allow a third contrast enhancement, which is scattering. A means for imaging the scatter signal as high contrast on a "black" background or field is to illuminate with light that is incident at an angle of incidence beyond that of the imaging objective lens, so only the signal scatter is collected. The image is analogous to that of fluorescence imaging where the illumination photons are rejected from the final image. Live cell imaging in 2D using dark-field microscopy is being conducted at Duke University, see, for example, Curry, A., Hwang, W. L., and Wax, A. (2006), "Epi-illumination through the microscope objective applied to dark-field imaging and microspectroscopy of nanoparticle interaction with cells in culture," Optics Express 14(14): 6535-6542.

Diffraction pattern measurement is a non-imaging technique that is complementary to the above imaging techniques which measure the spatial pattern in 3D of DNA, chromatin, proteins, and their specific labeling enhancements. Disease specific signatures of diffraction may be found at specific spatial frequencies, which are measured at specific scattering angles from the cell. Since the zero order light from the laser beam is orders of magnitude greater than the weakly scattered light from live cells, the technique of oblique illumination of the cell is proposed to greatly reduce this zero order light from reaching the optical detector or camera. This technique is similar to dark-field microscopy using nanoparticles as discussed above.

Examples of each of the techniques above may also be implemented as combinations using some general concepts described below. However, laboratory implementation will most likely be done as examples of the individual techniques for simplicity and lack of confounding variables during the development stage of live cell 3D imaging. Some examples of combining multiple imaging and measurement techniques are presented below.

Figure 6:
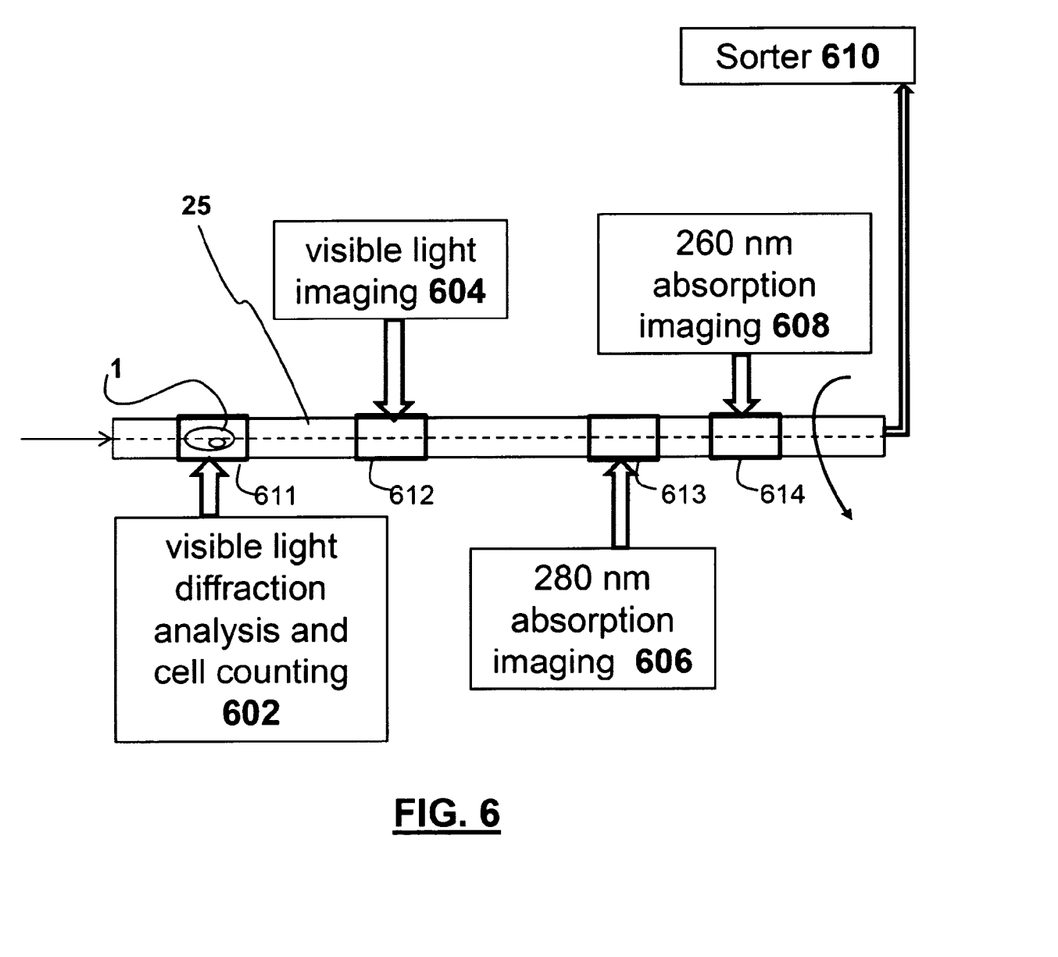
FIG. 6 schematically shows an optical tomography process including separate imaging stages along the same pathway.

Referring now to FIG. 6, an optical tomography process including separate imaging stages along the same pathway is shown. Separate imaging stages may be processed along the same pathway, such as a single microcapillary tube. For example, visible light diffraction analysis and cell counting 602 may be done at a first stage 611, followed by visible light imaging 604 at a second stage 612. In the case of imaging using live stains, 280 nm absorption imaging 606 may be conducted at a next stage 613, followed by 260 nm absorption imaging 608 at a fourth stage 614. For this example embodiment the cell should be aligned within the limited field of view at each stage as the cell continuously moves down a single rotating capillary tube. The 280 nm absorption imaging includes illuminating the object 1 with DUV light at a first wavelength in the range of about 275 nm to 285 nm. The 260 nm absorption imaging includes illuminating the object 1 DUV light at a second wavelength in the range of about 255 nm to 265 nm.

In another example, a single imaging stage that combines one or more image contrast mechanisms, such as absorption at wavelengths of 260 nm and 280 nm, measuring DUV absorption and native fluorescence, or measuring absorption at more than two visible wavelengths for one or more live stains. The components for combining optical imaging techniques can use multiple optical components for beam splitting and combining (dichroic or polarization beamsplitters) and possibly multiple cameras. Alternatively, a single camera and detection pathway can be used if the multiple excitation light sources are pulsed in time series or filter wheels or actual sources are physically moved or shuttered in time series. The single stage for imaging and measurement allow for stopped flow axial transport of the cells for precise alignment with the field of view.

In yet another example, dark-field imaging of live-cell stain with nanoparticle scatterers may advantageously be combined with oblique illumination of the cell with a laser for diffraction pattern analysis. This technique may be run at higher speeds and may be an initial stage before the slower and subsequent 3D imaging stage if initial results warrant a detailed 3D image of a particular cell.

In operation, the system provides an optical tomography process including separate imaging stages along the same pathway. A plurality of biological objects is transported along a pathway 25 to the first stage 611. At least one object of the plurality of objects is illuminated with visible light at the first stage to produce a diffraction pattern and the diffraction pattern is sensed by a light sensor. Using a computer program or equivalent, the diffraction pattern is analyzed to produce a diffraction analysis. At the second stage 612 the at least one object 1 is illuminated with visible light and the visible light emanating from the at least one object is sensed to produce a first plurality of pseudoprojection images. At the third stage 613 the at least one object 1 is illuminated with DUV light at a first wavelength and the DUV light at a first wavelength emanating from the at least one object is sensed to produce a second plurality of pseudoprojection images. At the fourth stage the at least one object is illuminated with DUV light at a second wavelength that is sensed to produce a third plurality of pseudoprojection images. Based on features derived from the first, second and third pluralities of pseudoprojection images and the diffraction analysis a plurality of objects may be sorted or otherwise classified using a sorter 610. The sorter 610 may be any of many types of conventional classifiers, usually embodied in software residing in a computer such as a statistical sorter, adaptive classifier, neural network or equivalents.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A system for 3D imaging of live cells in an optical tomography system comprising:
   a microfluidics cartridge including a tube positioned relative to a microscope objective, a conduit loop having a first port coupled to an entrance valve, a second port coupled to an exit valve, a semi-permeable membrane portion, a rotating portion and an imaging window;

where the rotating portion is mounted between a first fitting and a second fitting, where the first fitting couples the rotating portion to the entrance valve and the second fitting couples the rotating portion to the exit valve;

a rotation mechanism attached to the rotating portion;

a microscope objective located to view objects through the imaging window;

an axial translation mechanism coupled to the microscope objective;

a second conduit interfacing with the semi-permeable membrane, where the second conduit carries nutrients into the conduit loop and waste products out of the conduit loop;

at least one radiation source positioned to illuminate the imaging window including a biological object held therein, where the at least one radiation source generates radiation having a spectral bandwidth limited to wavelengths between 150 nm and 390 nm;

at least one sensor positioned to sense radiation transmitted through the biological object and the microscope objective;

an image processor coupled to receive data from the sensor; and a reconstruction module coupled to the image processor, where the reconstruction module processes the data to form a 3D image of the biological object.

2. The system of claim 1 wherein the nutrients include oxygen and a buffer.

3. The system of claim 1 wherein the axial translation mechanism comprises a piezoelectric transducer.

4. The system of claim 1 wherein the at least one radiation source comprises a computer-controlled light source and condenser lens assembly.

5. The system of claim 1 wherein a computer is linked to control the piezoelectric transducer, where the piezoelectric transducer axially moves the objective lens so as to extend the depth of field of the objective lens.

6. The system of claim 1 wherein the spectral bandwidth has wavelengths further limited to between 240 nm and 300 nm.

7. The system of claim 1 wherein the spectral bandwidth has wavelengths further limited to between 260 nm and 265 nm.

8. The system of claim 1 wherein the spectral bandwidth has wavelengths further limited to between 280 nm and 285 nm.

9. The system of claim 1, wherein the radiation stimulates native fluorescence from the live cell, further comprising measuring the stimulated fluorescence.

10. The system of claim 1, wherein a size of a voxel in the reconstructed 3D image is known, the reconstruction means further comprising a means for measuring a concentration of molecules absorbing the radiation by measuring the absorbance per voxel.

11. The system of claim 1 wherein the biological object includes a live cell.

12. The system of claim 1 wherein the microfluidics cartridge is contained in a temperature-controlled aqueous environment.

13. The system of claim 12 wherein the aqueous environment comprises physiological buffered saline.

14. The system of claim 1 wherein the sensed radiation includes imaging signals emanating from DNA.

15. The system of claim 1 wherein the sensed radiation includes imaging signals emanating from protein.

16. The method of claim 1 wherein the sensed radiation includes imaging signals emanating from hydrophilic surfaces.

17. The system of claim 1 wherein the generated radiation comprises multiple wavelengths.

18. The system of claim 1 wherein the reconstruction module processes the data using ratio imaging.

19. The system of claim 18 wherein the ratio imaging includes images formed from wavelengths ranging from 260 nm to 280 nm.

20. The system of claim 1 wherein the at least one radiation source comprises multiple sources for generating at least first and second selected wavelengths selected to enhance natural radiation absorbance by DNA.

21. The system of claim 1 wherein the spectral bandwidth is limited to wavelengths selected to enhance natural radiation absorbance by protein.

22. The system of claim 1 wherein the at least one radiation source comprises multiple sources transmitting at least two selected wavelengths that are pulsed in time series.

23. The system of claim 1 wherein the at least one radiation source comprises multiple sources transmitting at least two selected wavelengths.

24. The system of claim 1 wherein the sensor is an ultraviolet pixel array detector.

25. The system of claim 1 comprising a beamsplitter positioned to split radiation into at least two selected wavelengths.

26. The system of claim 25 wherein the beamsplitter is selected from the group consisting of a polarizing beam splitter, a Wollaston prism, a birefringent element, a half-silvered mirror, a 50/50 intensity beamsplitter, a dielectric optically coated mirror, a pellicle film and a dichroic mirrored prism.

27. The system of claim 1 wherein the at least one sensor comprises:
a first light detector positioned to receive light having a first wavelength; and
a second light detector sensitive to a second wavelength, the second light detector positioned to receive light having the second wavelength.

28. The system of claim 27 wherein the first light detector is sensitive to radiation having a wavelength matching the natural absorbance of human DNA.

29. The system of claim 27 wherein the second light detector is sensitive to radiation having a wavelength matching the natural absorbance of protein.

30. The system of claim 27 wherein the first light detector is sensitive to radiation having a wavelength that includes imaging signals emanating from hydrophilic surfaces.

31. The system of claim 1 further comprising at least one filter interposed between the at least one sensor and the transmitted radiation.

32. The system of claim 1 wherein the microfluidics cartridge and second conduit are enclosed in a temperature-controlled environment.

33. An optical tomography method including separate imaging stages along the same pathway comprising:
transporting a plurality of biological objects along a pathway to a first stage;
illuminating at least one object of the plurality of objects with visible light at the first stage to produce a diffraction pattern;
sensing the diffraction pattern;
analyzing the diffraction pattern to produce a diffraction analysis;
illuminating the at least one object with visible light at a second stage;

sensing visible light emanating from the at least one object to produce a first plurality of pseudoprojection images;
illuminating the at least one object with DUV light at a first wavelength at a third stage;
sensing the DUV light at a first wavelength emanating from the at least one object to produce a second plurality of pseudoprojection images;
illuminating the at least one object with DUV light at a second wavelength at a fourth stage;
sensing the DUV light at a second wavelength emanating from the at least one object to produce a third plurality of pseudoprojection images;
sorting the at least one object responsively to the first, second and third pluralities of pseudoprojection images and the diffraction analysis.

34. The method of claim 33 further comprising counting the biological objects.

35. The method of claim 33 wherein the plurality of biological objects comprise live cells.

36. The method of claim 33 wherein the DUV light at a first wavelength is in the range of 255 nm-265 nm.

37. The method of claim 33 wherein the DUV light at a second wavelength is in the range of 275 nm-285 nm.

38. The method of claim 33 wherein the diffraction pattern further comprises a dark-field imaging pattern.

* * * * *